(12) United States Patent
Loeb et al.

(10) Patent No.: US 6,522,827 B1
(45) Date of Patent: Feb. 18, 2003

(54) LASER DEVICES FOR PERFORMING A MYRINGOTOMY

(75) Inventors: Marvin P. Loeb, Huntington Beach, CA (US); L. Dean Crawford, Irvine, CA (US)

(73) Assignee: Trimedyne, Inc., Irvine, CA (US)

( * ) Notice: Subject to any disclaimer, the term of this patent is extended or adjusted under 35 U.S.C. 154(b) by 44 days.

(21) Appl. No.: 09/686,410

(22) Filed: Oct. 11, 2000

(51) Int. Cl.[7] .................................................. G02B 6/10
(52) U.S. Cl. ........................ 385/147; 385/137; 606/17
(58) Field of Search .............................. 385/147, 134, 385/902, 137; 606/17, 16, 15

(56) References Cited

U.S. PATENT DOCUMENTS

| | | | | |
|---|---|---|---|---|
| 5,280,378 A | * | 1/1994 | Lombardo | 369/199 |
| 5,709,677 A | * | 1/1998 | Slatkine | 606/17 |
| 5,807,242 A | * | 9/1998 | Scheller et al. | 385/117 |
| 5,951,543 A | * | 9/1999 | Brauer | 606/10 |
| 5,951,544 A | * | 9/1999 | Konwitz | 606/13 |
| 6,200,311 B1 | * | 3/2001 | Danek et al. | 606/15 |

* cited by examiner

*Primary Examiner*—Georgia Epps
*Assistant Examiner*—Richard Hanig
(74) *Attorney, Agent, or Firm*—Olson & Hierl, Ltd.

(57) ABSTRACT

A lasing device for performing a myringotomy or like procedure is provided. The distal end portion of an optical fiber used to transmit a laser energy beam to the surgical site is covered with a disposable, removably mounted sheath, whose distal end is substantially transparent to the wavelength of laser energy being emitted through the optical fiber. Optionally, a relatively low power aiming beam can be emitted coaxially with the laser energy beam.

59 Claims, 2 Drawing Sheets

LASER DEVICES FOR PERFORMING A MYRINGOTOMY

FIELD OF THE INVENTION

The invention relates to a medical device and, more particularly, to a lasing device for performing a myringotomy.

BACKGROUND OF THE INVENTION

Otitis media is the medical term for an infection of the middle ear, which is characterized by the build-up of fluid and pressure, causing significant pain in the ear. Otitis media occurs in adults, and more frequently in children, and seems to reoccur often in particular individuals. In the United States, otitis media in children results in an estimated 25 million physician office visits each year, representing 40% of all pediatric office visits, and the insertion of more than one million ear drainage tubes annually. In all, the overall cost of treating otitis media in the United States is approximately five billion dollars per year.

The treatment for otitis media currently involves the use of an antibiotic, such as amoxicillin, coupled with the use of a needle, lancet or blade which is used to puncture the ear drum or make an incision therein, to allow fluid to escape and the middle ear to aerate, i.e., a procedure commonly referred to as a myringotomy. This procedure frequently requires hospitalization and general anesthesia in children. However, because mechanical punctures have a tendency to heal and close in a few days, the buildup of fluid reoccurs and the pain caused by the pressure returns. To allow for continued drainage, the treatment for otitis media also currently involves the insertion of a tiny tympanotomy or drainage tube through the puncture to keep the puncture open and permit the continued flow of fluid and aeration of the surrounding ear drum area for a two to five week period. The tube is typically removed in a second visit to the physician. If the tube becomes clogged or falls out prematurely, another visit to the physician is required to clear or reinsert the tube, which necessarily increases the cost of treating the infection.

While a myringotomy can be performed by a general practitioner, family practitioner or pediatrician, it is often performed by an otorhinolaryngologist (ear, nose and throat specialist), which necessarily entails the incurment of substantial professional fees.

Thus, there remains a need for a device which can be used in a medical office by a family or general practitioner or pediatrician to create a puncture, which will remain open and will not require the insertion of a separate tube, eliminating the need for a second office visit. There is also a need for a device which will create a puncture in a matter of a few seconds without any hospitalization or general anesthesia. Still further, there is a need for a device which does not need to be sterilized prior to or after performing the myringotomy procedure.

SUMMARY OF THE INVENTION

The present invention contemplates a lasing device adapted to create a long lasting (two to five week) puncture in the ear drum for treating otitis media and other like middle ear infections, and eliminating the need for hospitalization, general anesthesia, repeat office visits and the sterilization of the laser device prior to or after use.

The lasing device comprises a laser energy conduit, such as a fiber optic, with a proximal end adapted for coupling to a laser energy source and a distal end portion covered by a removable sheath whose distal end is substantially transparent to the laser energy being emitted through the distal end of the conduit.

In one embodiment, a pocket in the distal end portion of the sheath receives a lens which diverges the beam of laser energy emitted from the conduit.

In another embodiment, the sheath includes a body portion that terminates in a cap integrally connected to the body portion and transparent to the laser energy emitted through the conduit.

In yet another embodiment, the sheath includes an inner surface which defines an opening in the distal end portion thereof and a film cap which covers the opening; the film insert is transparent to the laser energy being emitted through the conduit.

In a preferred embodiment, the sheath includes a heat-shrinkable plastic whose distal end is heat shrunk over a relatively short cylinder of quartz or fused silica. The distal end surface of the cylinder can be sandblasted and/or carbon coated, if desired. One aspect of the present invention is directed to a mounting structure for the sheath to the conduit. In one specific embodiment, ribs on the inner surface of the sheath create a friction engagement with the outer surface of the conduit. In another embodiment, the conduit outer surface and the sheath inner surface define a plurality of spaced-apart, complementary and flexible ribs which coact to hold the sheath over the conduit and portion during use. In another embodiment, the ribs are located on the conduit and abut against the inner surface of the sheath. In yet another embodiment, the ribs on the conduit are received in grooves in the inner surface of the sheath.

Other features and advantages of the present invention will become readily apparent from the following detailed description, the appended drawings, and the accompanying claims.

DETAILED DESCRIPTION OF THE PREFERRED EMBODIMENTS

Figure 1:
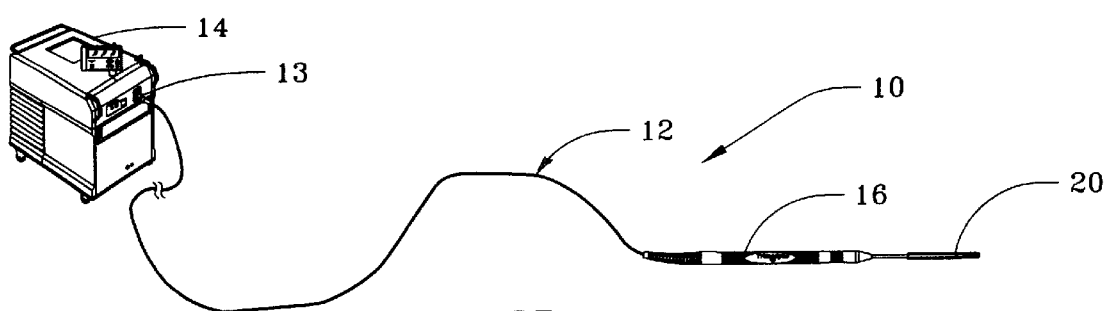
FIG. 1 is a simplified perspective view of the laser device of the present invention.

The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

For ease of description, the sheath and optical fiber of the laser device embodying the present invention are described hereinbelow in their usual generally horizontal use orientation and terms such as upper, lower, vertical, etc., will be used herein with reference to this usual position.

Moreover, the FIGURES omit details of the lasing device structure such as, for example, the laser source, the handpiece and the structure of the optical fiber, all of which are known in the art and will be recognized by those skilled in the art as such. The detailed descriptions of such elements are not necessary to an understanding of the invention. Accordingly, such elements are herein represented only to the degree necessary to aid an understanding of the features of the present invention.

Referring now to the drawings and, more particularly, to FIG. 1, there is shown therein a laser device 10 constructed in accordance with the present invention which includes an elongate, generally cylindrically shaped optical fiber or laser energy conduit 12 having a proximal end 13 which is optically coupled to a source of laser energy 14 and a distal end portion 15 (FIG. 2) extending through a handpiece 16. Sheath 20, whose distal end is transparent to the wavelength of laser energy being used, is removably disposed over the distal end portion of laser energy conduit 12.

The laser source 14 may be any suitable laser including, but not limited to, a excimer, argon, KTP, diode, Nd:YAG, Holmium:YAG, Erbium:YAG or carbon dioxide ($CO_2$) laser. The optical fiber 12 may comprise a single fiber having a core diameter of 200 to 1000 microns, preferably about 365 to 600 microns. Alternatively, the fiber 12 can be made of a plurality of smaller optical fibers bound together in a bundle. Optical fibers with a relatively high hydroxyl (OH) content may be used with excimer lasers. Optical fibers with the usual normal OH content can, for example, be used with argon, KTP and Nd:YAG lasers. Optical fibers with a relatively low or extremely low OH content may be used with Holmium or Erbium lasers, respectively. A hollow waveguide can also be used to transmit Erbium laser energy, as well as $CO_2$ laser energy, for this purpose.

A relatively low power (about 5 milliwatts) aiming beam, for example a red Helium-Neon (He—Ne) aiming beam, can be delivered coaxially with the relatively higher power (1 to 20 watt, preferably 2 to 20 watt) laser energy beam used to pierce the ear drum.

Figure 2:
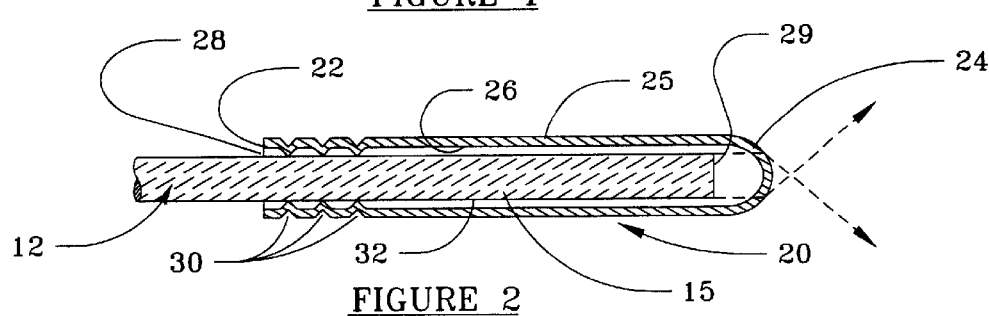
FIG. 2 is a vertical cross-sectional view of one embodiment of the sheath and optical fiber of the laser device of FIG. 1.

As shown in FIG. 2, a sheath 20 is removably secured over the distal end portion 15 of the optical fiber 12. FIG. 2 depicts an embodiment where the sheath 20, including an open proximal end 22, is provided with a closed distal end 24 and an elongate and generally cylindrically shaped hollow body 25 therebetween. The sheath 20 includes a generally cylindrical interior surface 26 defining a cavity and an opening 28 in the proximal end 22 which allows the sheath 20 to be slid over and around the elongate distal end portion 15 of the optical fiber 12, into a relationship where the body portion 25 of the sheath 20 surrounds the distal end portion 15 of the optical fiber 12 and the closed end 24 of the sheath 20 is disposed forward of, and spaced from, the generally vertical distal end face 29 of the optical fiber 12. A plurality of spaced-apart and parallel flexible ribs 30 extend outwardly from, and circumferentially about, the interior surface 26 of the sheath 20 adjacent the proximal end 22 thereof in an orientation generally transverse to the longitudinal axis of the sheath 20. As shown in FIG. 2, the tips of the ribs 30 are adapted to frictionally engage the outer surface 32 of the optical fiber 12 and hold the sheath 20 over the optical fiber 12 during use of the laser device 10.

The sheath 20 is about two to twenty centimeters in length, preferably about four to twelve centimeters in length, with an inside diameter slightly larger than the outside diameter of the optical fiber 12. The body 25 portion of the sheath 20 may be made of any plastic material that is biocompatible in contact with tissue for a short period of time, including materials such as latex, silicone rubber, fluorocarbon polymers (Teflon), polyvinyl chloride, polyurethane, copolyester polymers such as polyethylene terephthalate (PET), thermoplastic rubbers, silicon-polycarbonate copolymers, a polyolefin such as polyethylene and polypropylene, ethyl-vinyl-acetate copolymers, polyamides, polyisoprene, or combinations thereof, and other materials known in the art. Particularly preferred are polyethylene terephthalate, polytetrafluorsethylene, polyethylene, and silicone rubber.

The sheath 20 may be made by such methods, for example, as injection or blow molding, using a polyolefin such as polyethylene or polypropylene, a polystyrene, an acrylic, resin, acrylonitrile-butadiene-styrene (ABS), nylon; thermoforming, using a polypropylene or polyethylene terephthalate; polycarbonate, ABS or PETG; heat shrinkage, using a fluorocarbon or polyethylene terephthalate; extrusion, using a nylon, polyvinyl chloride resin, pebax, a fluorocarbon resin, polystyrene or polycarbonate; or dipping, using silicone rubber, latex, or polyurethane.

The closed distal end 24 of the sheath 20 shown in FIG. 2 can be comprised of the same material as the body portion 25 or of a dissimilar material which is substantially transparent to the wavelength of laser energy to be transmitted therethrough. Arrows in FIG. 2 indicate an approximate path of laser energy emission. Using a HeNe aiming beam as described hereinabove, the physician can determine the approximate size of the opening to be produced in the ear drum by adjusting the spacing between the end face 24 of sheath 20 and the ear drum, or by moving the device in a circular pattern. An aperture having a diameter larger than the diameter of the optical fiber 12 can be formed in this manner.

In accordance with the present invention, the use of disposable sheath 20 over the optical fiber 12 eliminates the need to sterilize the entire optical fiber 12, usually about two or three meters long, and handpiece 16 which, under normal circumstances, could be contaminated by the backscatter of blood and cellular debris during the lasing procedure.

Figure 3A:
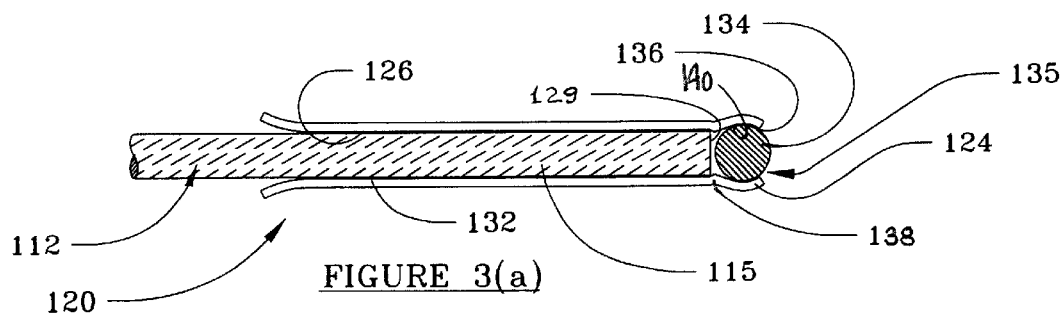
FIG. 3 is a vertical cross-sectional view of a second embodiment of the sheath and optical fiber of the laser device of FIG. 1.

FIGS. 3(a) and (b) depict an alternate sheath embodiment 120. Sheath 120 differs in structure from the sheath 20 in that the sheath 120 includes an open distal end 124 which receives a quartz or fused silica ball lens 134, which serves to converge and then diverge the beam of laser energy being emitted through the distal end face 129 of the optical fiber 112 and allows the creation of a puncture in the ear drum larger than the diameter of the optical fiber 112. The lens 134 also protects the optical fiber 112 from backsplash of blood and cellular debris during use of the laser device.

The lens 134 is shown in the form of a ball and can be made of any suitable quartz, fused silica or other material which has either a low, normal, or high OH content which allows the transmission of the wavelengths of laser energy produced by the types of lasers described above. Lens 134 can also consist of a calcium chloride crystal or sapphire, if $CO_2$ laser energy is employed through a hollow waveguide, as known in the art. Lens 134 can also be a cylindrical segment of a quartz or fused silica rod, about 2 to 10 millimeters in length, preferably about 3 to 8 millimeters in length. The diameter of lens 134 can vary. If desired, a portion of the lens 134 can be sandblasted, preferably the distal end portion. Alternatively, the distal end portion of lens 134 can be provided with a carbon coating.

As shown in FIG. 3(a), the lens 134 is seated in a generally circularly shaped pocket 135 which is formed in the open distal end 124 of the sheath 120. Pocket 135 is defined by a rib 138 which extends outwardly from, and circumferentially around, the interior surface 126 of the sheath 120 and a curved portion 140 of the interior surface 126 of the sheath 120 which extends between the rib 138 and the peripheral distal edge 136 of the sheath 120. The portion 140 is generally curved and shaped to receive the spherically shaped ball lens 134 in a relationship where one end of the lens 134 is positioned in abutting relationship with the rib 138, the top, bottom and side portions of the lens 134 are positioned in abutting relationship with the interior surface portion 140 of the sheath 120 and the opposite end of the lens 134 protrudes slightly past the peripheral edge 136 of the sheath 120. Optionally, a ceramic sleeve can surround lens 134 in a manner similar to that shown for rod 624 in FIG. 8.

As also shown in FIG. 3(a), the inside diameter of sheath 120 is only slightly larger than the outside diameter of optical fiber 112 so that sheath 120 is removably retained in place by a friction fit. Alternatively, sheath 120 can be made of a heat shrinkable plastic tube and fixed in place by heat shrinking over an appropriately shaped mandrel, with lens 134 positioned opposite the distal end of the mandrel, within the distal end of sheath 120.

Figure 3B:
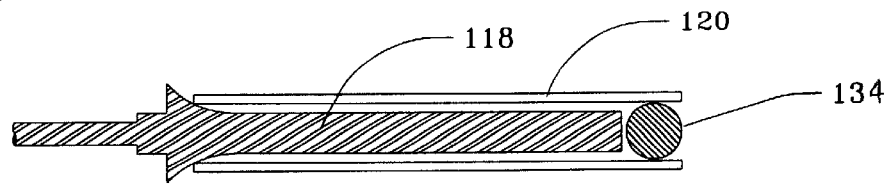

As seen in FIG. 3(b), prior to heat shrinking, sheath 120 is positioned over mandrel 118, which may be made of metal, wood or plastic, and lens 134. Mandrel 118 can contain grooves or depressions, to create the ribs in sheath 120 described in FIG. 2 above.

Figure 4:
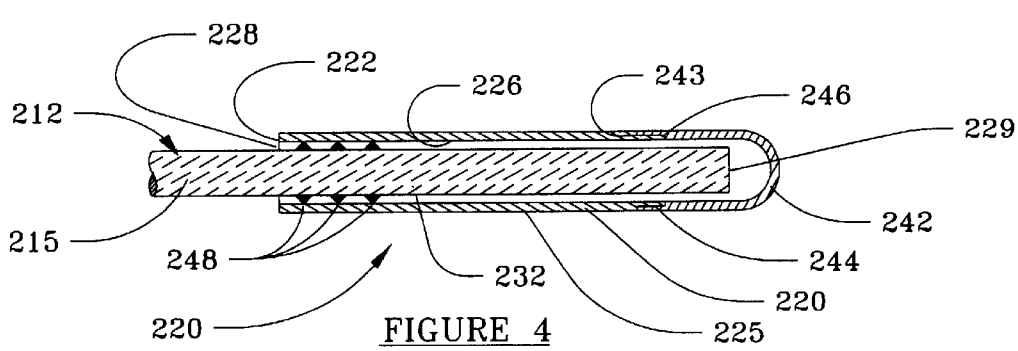
FIG. 4 is a vertical cross sectional view of another embodiment of the sheath and optical fiber of the laser device of FIG. 1.

FIG. 4 illustrates another sheath embodiment 220 where the closed distal end portion thereof comprises a cap 242 integrally secured to, and extending outwardly from, the end of the body 225 of the sheath 220. Particularly, in this embodiment, sheath body 225 includes an open distal end 243 incorporating a complementary tongue and groove structure 244 which extends circumferentially around the periphery thereof. The cap 242 includes an open proximal end incorporating a tongue and groove structure 246 extending circumferentially around the periphery thereof which is adapted to complement and cooperate with the tongue and groove structure 244 on sheath body 225 to allow the integral connection of the cap 242 to the sheath body 225. It is understood, of course, that the tongue and groove structure disclosed herein is but one of the means known in the art which fall within the scope of this invention for connecting the two parts.

The sheath body 225 may be made from an inexpensive plastic material which can be easily manufactured by injection or blow molding, vacuum forming, heat shrinking, dipping or other means known in the art and which is not transparent to the wavelength of laser energy being emitted through the optical fiber 212. Cap 242, on the other hand, can be made from quartz, fused silica, a polycarbonate, acrylic or other material dissimilar to the material of sheath body 225, as also known in the art, which is substantially transparent to the wavelength of laser energy being emitted through the end of optical fiber 212.

The optical fiber 212 differs in structure from the optical fiber 12 shown in FIG. 2 in that optical fiber 212 includes a plurality of ribs 248 extending outwardly from, and circumferentially about, the outer surface 232 thereof in a spaced-apart and parallel relationship generally transverse to the longitudinal axis of the optical fiber 212. The ribs 248 are positioned on the optical fiber 212 in a relationship such that the tips thereof abut and frictionally engage against the interior surface 226 of the sheath 220 adjacent the proximal end 222 thereof to hold the sheath 220 over the distal end portion 215 of the optical fiber 212 during use. Ribs 248 can be made by heat shrinking loops of suitable plastic material about optical fiber 212, by winding a thin strand of plastic monofilament (e.g., a fishing line) around a portion of the optical fiber 212 and securing the strand to the exterior of fiber 212 by adhesive bonding, thermal bonding, and the like.

Figure 5:
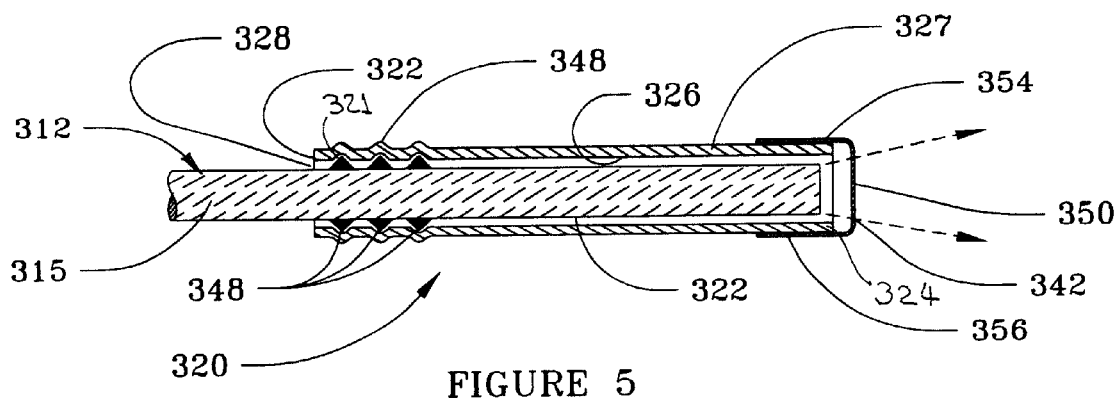
FIG. 5 is a vertical cross sectional view of yet another embodiment of the sheath and optical fiber of the laser device of FIG. 1.

FIG. 5 depicts yet a further embodiment of an optical fiber 312 and a sheath 320 where the optical fiber 312 includes a plurality of ribs 348 similar in structure and orientation to the ribs 248 on the optical fiber 212 shown in FIG. 4. The sheath 320 includes a plurality of spaced-apart, parallel, and circumferential grooves 321 extending into the interior surface 326 thereof adjacent the proximal end 322 thereof. In accordance with the present invention, the ribs 348 on the optical fiber 312 are adapted to be seated into the corresponding grooves 321 in the sheath 320 when the sheath 320 is slid over the distal end portion 315 of the optical fiber 312 for removably securing and holding the sheath 320 over the optical fiber 212 during use of the laser device.

As also shown in FIG. 5, the sheath 320 includes an open distal end 324 which is covered by a cap of film material 342 including a central portion 350 positioned over and covering the opening 352 and diametrically opposed end portions 354 and 356 secured to diametrically opposed sides of the outer surface 327 of the sheath 320. The sheath 320 is made of the same type of material as the body 225 of the sheath 220 shown in FIG. 4 while the film 342 is made of a material which is substantially transparent to the wavelength of laser energy being emitted from the optical fiber 312 such as, for example, a thin film of latex or other plastic material. The film 342 may be attached to the distal end 324 of the sheath 320 by heat shrinkage, an adhesive, thermal bonding or other means. Moreover, it is understood that the film 342 may be of any suitable shape such as, for example, a campanulate or dome shaped insert which telescopes the end 324 of the sheath 320. Laser energy emitted from optical fiber 312 and passing through cap 342 diverges slightly, usually about 5 to 15 degrees, depending upon the numerical apertures and optical indices of the respective materials and the wavelength of the laser energy beam. The approximate path of the emitted laser energy beam is shown by arrows.

Figure 6:
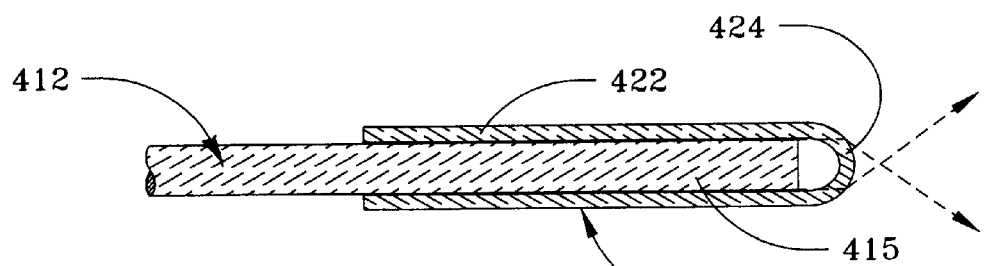
FIG. 6 is a cross-sectional view showing an embodiment of the present invention where the sheath is a capillary tube.

FIG. 6 illustrates an embodiment where sheath 420 is a capillary tube 422 made of quartz or fused silica. Distal end 424 of tube 422 is closed and formed into a rounded shape by heat as is well known in the art. The rounded shape permits manipulation in a manner similar to that described for the embodiment of FIG. 2. Alternatively, sheath 420 can be made from a transparent plastic rod by creating a blind bore hole sized to receive optical fiber 412. The blind bore hole can extend to within 1 to 8 millimeters of the distal end of the plastic rod. The external portion of such a plastic rod can be rounded, as desired, to a shape similar to that shown in FIG. 6. Other expedients can be utilized as well to manufacture the sheath 420, the ultimate choice being determined largely by cost considerations.

Figure 7:
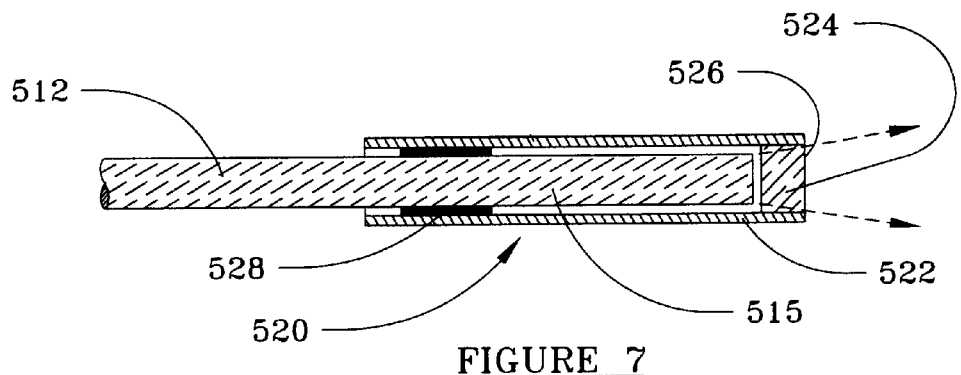
FIG. 7 is a cross-sectional view showing a further embodiment of the present invention with a quartz or fused silica end piece provided at the distal end of the optical fiber.

Yet another embodiment of the present invention is shown in FIG. 7. Sheath 520 is a sleeve with an inside diameter somewhat larger than that of optical fiber 512. A relatively short (about 2 to 10 millimeters, preferably about 3 to 8 millimeters) segment of a cylindrical rod 524, made from quartz or fused silica, is positioned within the distal end portion of sheath 520. Sheath 520 can be made of Teflon®, which can be heat shrunk about rod 524. Alternatively, sheath 520 can be a plastic tube with rod 524 affixed by an adhesive (not shown) within the distal end portion of sheath 520.

While sheath 520 can be formed by heat shrinking with ribs, as described above, to engage fiber 512, a heat shrunk plastic band or a piece of adhesive tape can provide a retainer 528 that provides a friction fit between optical fiber 512 and sleeve 520 when the latter is introduced over the distal end portion of the former. End face 526 of rod 524 is shown as flat, but can be rounded or any other shape. As a result, the path of laser energy beam emission diverges somewhat as shown by the arrows. In a most preferred embodiment, which requires less laser energy, end face 526 of rod 524 has been carbon coated or sandblasted, or both. End face 526 rapidly heats to a temperature exceeding 400° C. and vaporizes the eardrum in contact therewith in an instant.

In a test in air, continuous wave Nd:YAG laser energy (about 5 watts, 1064 nm wavelength) was transmitted for 2 seconds through a 550μ core diameter optical fiber, which had a 4 mm long, 1 mm core diameter fiber-optic cylinder with a sandblasted distal end face affixed to the distal end of the optical fiber by a heat shrunk cannula, as shown in FIG. 7. The temperature of the distal end face of the cylinder reached 845° C. However, the temperature of the heat shrunk sheath overlying the cylinder was only 50° C., less than the temperature at which tissue coagulation and damage occurs.

Figure 8:
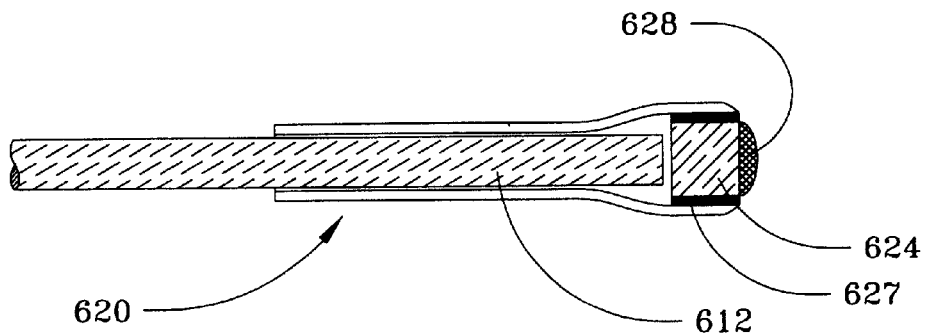
FIG. 8 is a cross-sectional view showing a further enhanced embodiment of the device of FIG. 7, where a ceramic sleeve is interposed between the quartz or fused silica end piece and the sheath, and the end piece has a rounded distal end.

FIG. 8 shows a further embodiment of the device of FIG. 7. To prevent heat from radiating laterally from sheath 620 and underlying cylindrical rod 624, a ceramic sleeve 627 is attached to the outer surface of rod 624 by an adhesive or the like. Ceramic sleeve 627 prevents thermal damage to sheath 620 and the sensitive cilia of the ear canal, if sheath 620 comes into contact therewith.

In this embodiment, cylindrical rod has a rounded or convex atraumatic end face 628, which can act as a lens, as seen in FIG. 6, and preferably, is sandblasted or provided with a carbon coating, or both, as shown in FIG. 8.

In use, a plurality of any one of the various embodiments depicted in the foregoing FIGURES are contained and stored in a cardboard or plastic box (not shown), with the open proximal ends thereof facing the top cover of the box. The top of the box is then opened, the distal end of the optical fiber is inserted into the proximal end of a sheath, which becomes frictionally engaged thereto. Engagement between the sheath and the optical fiber allows the sheath to be removed from the box without manually touching the sheath.

The sheath, disposed over the distal end of the optical fiber, is then inserted into the ear canal and advanced up to the ear drum through an otoscope (not shown) such as, for example, the Hotchkiss Otoscope marketed and sold by Preferred Products of Sam Rafael, Calif., or through a binocular microscope (not shown) such as, for example, the OPMI Series ENT Operating Microscopes marketed and sold by Carl Zeiss of Oberkochen, Germany, or under direct vision. Laser energy is then emitted from the distal end of the optical fiber and through the transparent or carbon coated/sandblasted end of the respective sheath embodiment to create a two to six millimeter aperture in the ear drum, preferably about two to about four millimeters in diameter. The distal end portion of the device embodying the present invention can be shifted back and forth or moved in a circular pattern relative to the ear drum to achieve this result, as described hereinabove. Only a few watts of laser energy, one to twenty watts, preferably two to ten watts, for one to twenty seconds, preferably about two to ten seconds, enables the creation of the two to four millimeter puncture. Once the puncture has been created, the optical fiber and sheath are removed from the otoscope, microscope, or the ear canal, and the sheath is disengaged from the end of the optical fiber by applying finger pressure against the proximal end of the sheath to break the friction bond between the sheath and the optical fiber and to slide the sheath off the end of the optical fiber for disposal.

In accordance with the present invention, the laser puncture is created, without bleeding, relieves the fluid pressure within and aerates the middle ear, which stays open for two to five weeks, and heals without scar tissue being visible five weeks or more after the procedure.

Numerous variations and modifications of the embodiments described above may be effected without departing from the spirit and scope of the novel features of the invention. It is to be understood that no limitation with respect to the specific embodiments illustrated herein is intended or should be inferred. It is, of course, intended to cover by the appended claims all such modifications as fall within the scope of the claims.

We claim:
1. A lasing device comprising a laser energy conduit adapted for connection to a laser energy source and including a proximal end for coupling to the laser energy source and a distal end covered by a removable sheath with a distal end portion which is substantially transparent to the wave length of the laser energy emitted through said distal end of said conduit.

2. A lasing device comprising a laser energy conduit adapted for connection to a laser energy source and including a proximal end for coupling to the laser energy source and a distal end covered by a removable sheath with a distal end portion which is substantially transparent to the wave length of the laser energy emitted through said distal end of said conduit, wherein said distal end portion of said sheath defines a pocket, and a lens for diverging the beam of laser energy emitted from said conduit is held in said pocket.

3. The lasing device of claim 2 wherein a ceramic sleeve surrounds the lens held in said pocket.

4. The lasing device of claim 2 wherein an exterior portion of the lens is sandblasted.

5. The lasing device of claim 2 wherein a distal end portion of the lens is provided with a carbon coating.

6. The lasing device of claim 2 wherein said pocket is adapted to receive a generally spherically shaped lens.

7. The lasing device of claim 6 wherein said sheath includes an inner surface defining an opening in said distal end portion and a rib extending outwardly from said inner surface adjacent to and spaced from said opening, said lens being received in said pocket between said rib and said opening.

8. The lasing device of claim 1 wherein said sheath includes a body and said distal end portion comprises a cap integrally connected to said body.

9. The lasing device of claim 8 wherein said body and said cap of said sheath include cooperating tongue and groove structures for coupling said cap to said body of said sheath.

10. The lasing device of claim 1 wherein said sheath includes an inner surface defining an opening in said distal end portion thereof and a film cap covering said opening and transparent to the laser energy being emitted from said conduit.

11. The lasing device of claim 1 wherein one of said sheath or said conduit includes at least one rib formed thereon for frictionally engaging and holding said sheath over said conduit.

12. The lasing device of claim 11 wherein said conduit includes an outer surface and said sheath includes an inner surface, each of which defines a plurality of spaced-apart ribs for frictionally engaging and holding said sheath over said conduit.

13. The lasing device of claim 11 wherein said sheath includes an inner surface end and said conduit includes an outer surface and a plurality of spaced-apart ribs extending outwardly therefrom and abutting said inner surface of said sheath for holding said sheath over said conduit.

14. A lasing device comprising a laser energy conduit adapted for connection to a laser energy source and including a proximal end for coupling to the laser energy source and a distal end covered by a removable sheath with a distal end portion which is substantially transparent to the wave length of the laser energy emitted through said distal end of said conduit, wherein one of said sheath or said conduit includes at least one rib formed thereon for frictionally engaging and holding said sheath over said conduit, and wherein said sheath includes a proximal end and an inner surface having a plurality of grooves formed therein, said conduit including an outer surface having a plurality of ribs extending outwardly therefrom and received in said grooves respectively for removably securing said sheath over said conduit.

15. A laser device comprising a fiber optic conduit adapted for coupling to a source of laser energy and a hollow sheath covering the distal end of said conduit and removably retained thereon, said sheath including a distal end portion substantially transparent to the laser energy emitted from said conduit.

16. The laser device of claim 15 wherein said distal end portion of said sheath defines a pocket; and a lens for diverging the laser energy emitted from said conduit is situated in said pocket.

17. The laser device of claim 16 wherein a ceramic sleeve surrounds the lens situated in said pocket.

18. The laser device of claim 16 wherein an exterior portion of the lens is sandblasted.

19. The laser device of claim 16 wherein a distal end portion of the lens is provided with a carbon coating.

20. The laser device of claim 16 wherein said pocket is adapted to receive a generally spherically shaped lens.

21. The laser device of claim 15 wherein said distal end portion of said sheath includes a cap substantially transparent to the laser energy emitted from said conduit.

22. The laser device of claim 15 wherein said sheath includes an inner surface defining an opening in said distal end portion thereof and a film cap covering said opening and comprising a material transparent to the laser energy emitted from said conduit.

23. The laser device of claim 15 wherein said conduit includes an outer surface and said sheath includes an inner surface, both having a plurality of coacting ribs for removably securing said sheath over said conduit.

24. The laser device of claim 15 wherein said sheath includes an inner surface and said conduit includes an outer surface having a plurality of ribs extending outwardly therefrom and abutting said inner surface of said sheath for removably securing said sheath over said conduit.

25. The laser device of claim 15 wherein the inner surface of the sheath has at least one circumferential rib for frictionally engaging and removably securing said sheath over said conduit.

26. The laser device of claim 15 wherein said sheath is a capillary tube with a closed distal end.

27. The laser device of claim 15 wherein said sheath is removably retained by friction fit.

28. A laser device comprising a fiber optic conduit adapted for coupling to a source of laser energy and a hollow removable sheath covering the distal end of said conduit and removably retained thereon, said sheath including a distal end portion defining a pocket, and wherein a segment of a cylindrical rod material transparent to the wave length of laser energy is situated in the pocket.

29. The laser device of claim 28 wherein the distal end face of the rod material is sandblasted.

30. The laser device of claim 28 wherein the distal end face of the rod is provided with a carbon coating.

31. The laser device of claim 28 wherein the distal end face of the rod is convex and is provided with a carbon coating.

32. The laser device of claim 28 wherein the distal end face of the rod is rounded.

33. The laser device of claim 28 wherein said rod is composed of a material selected from quartz, fused silica, or synthetic sapphire.

34. The laser device of claim 28 wherein said material is fused silica.

35. The laser device of claim 28 wherein a ceramic sleeve surrounds the exterior of the cylindrical rod.

36. A method of performing a myringotomy which comprises the steps of removably mounting a sheath transparent to laser energy onto a fiber optic;

passing a laser energy beam through said fiber optic and said sheath and projecting said beam onto an ear drum to be perforated; and maintaining incidence of the projected beam onto the ear drum for a time period sufficient to perforate the ear drum.

37. The myringotomy method in accordance with claim 36 wherein the laser energy beam has power output in the range of about 1 to about 20 watts.

38. The myringotomy method in accordance with claim 36 wherein the laser energy beam has power output in the range of about 2 to about 10 watts.

39. The myringotomy method in accordance with claim 36 wherein a relatively lower power aiming beam is projected onto the ear drum coaxially with the laser energy beam.

40. The myringotomy method in accordance with claim 39 wherein the aiming beam is a red helium-neon laser beam.

41. A lasing device comprising a source of laser energy, a laser energy conduit including a proximal end adapted for connection to the laser energy source, a distal end covered by a removable sheath defining a pocket, and a lens transparent to the wave length of laser energy for directing the beam of laser energy emitted from said conduit held in said pocket.

42. The lasing device of claim 41 wherein a ceramic sleeve surrounds the lens held in said pocket.

43. The lasing device of claim 41 wherein an exterior portion of the lens is sandblasted.

44. The lasing device of claim 41 wherein a distal end portion of the lens is provided with a carbon coating.

45. The lasing device of claim 41 wherein said pocket is adapted to receive a generally spherically shaped lens.

46. The lasing device of claim 45 wherein said sheath includes an inner surface defining an opening in said distal end portion and a rib extending outwardly from said inner surface adjacent to and spaced from said opening, said lens being received in said pocket between said rib and said opening.

47. The lasing device of claim 41 wherein the lens is composed of a material selected from quartz, fused silica and synthetic sapphire.

48. A lasing device comprising a laser energy conduit adapted for connection to a laser energy source and including a proximal end for coupling to the laser energy source and a distal end covered by a removable sheath with a distal end portion which is substantially transparent to the wave length of the laser energy emitted through said distal end of said conduit, wherein one of said removable sheath or said conduit includes at least one rib formed thereon for frictionally engaging and holding said sheath over said conduit.

49. The lasing device of claim 48 wherein said removable sheath includes a proximal end and an inner surface having a plurality of grooves formed therein, said conduit including an outer surface having a plurality of ribs extending outwardly therefrom and received in said grooves respectively for removably securing said sheath over said conduit.

50. A laser device comprising a fiber optic conduit adapted for coupling to a source of laser energy and a hollow removable sheath covering the distal end of said conduit and removably retained thereon, said sheath including a distal end portion defining an pocket and wherein a segment of a cylindrical rod material transparent to the wave length of laser energy is situated in the pocket.

51. The laser device of claim 50 wherein the distal end face of the rod material is sandblasted.

52. The laser device of claim 50 wherein the distal end face of the rod is provided with a carbon coating.

53. The laser device of claim 50 wherein the distal end face of the rod is convex and is provided with a carbon coating.

54. The laser device of claim 50 wherein the distal end face of the rod is rounded.

55. The laser device of claim 50 wherein said rod is composed of a material selected from quartz, fused silica and synthetic sapphire.

56. The laser device of claim 50 wherein a ceramic sleeve surrounds the exterior of the cylindrical rod.

57. The lasing device of claim 2 wherein the lens is composed of a material selected from quartz, fused silica, or synthetic sapphire.

58. A lasing device comprising a laser energy conduit adapted for connection to a laser energy source and including a proximal end for coupling to the laser energy source and a distal end covered by a removable sheath with a distal end portion which is substantially transparent to the wave length of the laser energy emitted through said distal end of said conduit, wherein one of said sheath or said conduit includes at least one rib formed thereon for frictionally engaging and holding said sheath over said conduit.

59. A lasing device comprising a laser energy conduit adapted for connection to a laser energy source and including a proximal end for coupling to the laser energy source and a distal end covered by a removable sheath with a distal end portion which is substantially transparent to the wave length of the laser energy emitted through said distal end of said conduit, wherein said sheath includes a proximal end and an inner surface having a plurality of grooves formed therein, said conduit including an outer surface having a plurality of ribs extending outwardly therefrom and received in said grooves respectively for removably securing said sheath over said conduit.

* * * * *